United States Patent

Marlow et al.

[11] Patent Number: 5,868,694
[45] Date of Patent: Feb. 9, 1999

[54] LOWER BACK SUPPORT APPARATUS

[76] Inventors: Bobby Marlow, Rte. 1, Box 3148; Eulis C. Hatfield, Rte. 1, Box 3178, both of Duff, Tenn. 37729

[21] Appl. No.: 893,417

[22] Filed: Jul. 11, 1997

[51] Int. Cl.$^6$ ...................................................... A61F 5/00
[52] U.S. Cl. .................................. 602/32; 602/36; 602/19
[58] Field of Search ................................. 602/32, 34, 36, 602/19, 33, 38–40; 606/240, 241, 242

[56] References Cited

U.S. PATENT DOCUMENTS

| | | | |
|---|---|---|---|
| 3,003,498 | 10/1961 | Hotas | 602/32 |
| 3,167,068 | 1/1965 | Carr | 602/36 |
| 4,802,667 | 2/1989 | Altner . | |
| 4,991,572 | 2/1991 | Chases . | |
| 5,224,924 | 7/1993 | Urso | 602/19 |
| 5,387,183 | 2/1995 | Jones . | |
| 5,388,274 | 2/1995 | Glover et al. . | |
| 5,403,270 | 4/1995 | Schipper | 602/36 |
| 5,403,271 | 4/1995 | Saunders et al. . | |
| 5,421,809 | 6/1995 | Rise . | |
| 5,462,518 | 10/1995 | Hatley et al. | 602/36 |
| 5,704,881 | 1/1998 | Dudley | 602/36 X |

FOREIGN PATENT DOCUMENTS

| | | | |
|---|---|---|---|
| 8803013 | 5/1988 | WIPO | 602/36 |

*Primary Examiner*—Richard J. Apley
*Assistant Examiner*—Denise Pothier
*Attorney, Agent, or Firm*—Pitts & Brittian, P.C.

[57] ABSTRACT

A lower back support apparatus for supporting the user's lower back when seated. The lower back support apparatus includes a support frame and a support belt which is supportable on the frame. The support belt defines a belt portion and straps secured to the belt portion. The belt portion is securable around the waist of a user, and the straps extend from the belt portion and are configured to fit securely on the shoulders of the user. The straps carry two rings one each positionable at each shoulder. The support frame is configured to releasably secure to a seat. Two spring and hook assemblies mounted on opposing sides of the support frame and each includes a hook for hooking onto each of the rings.

4 Claims, 3 Drawing Sheets

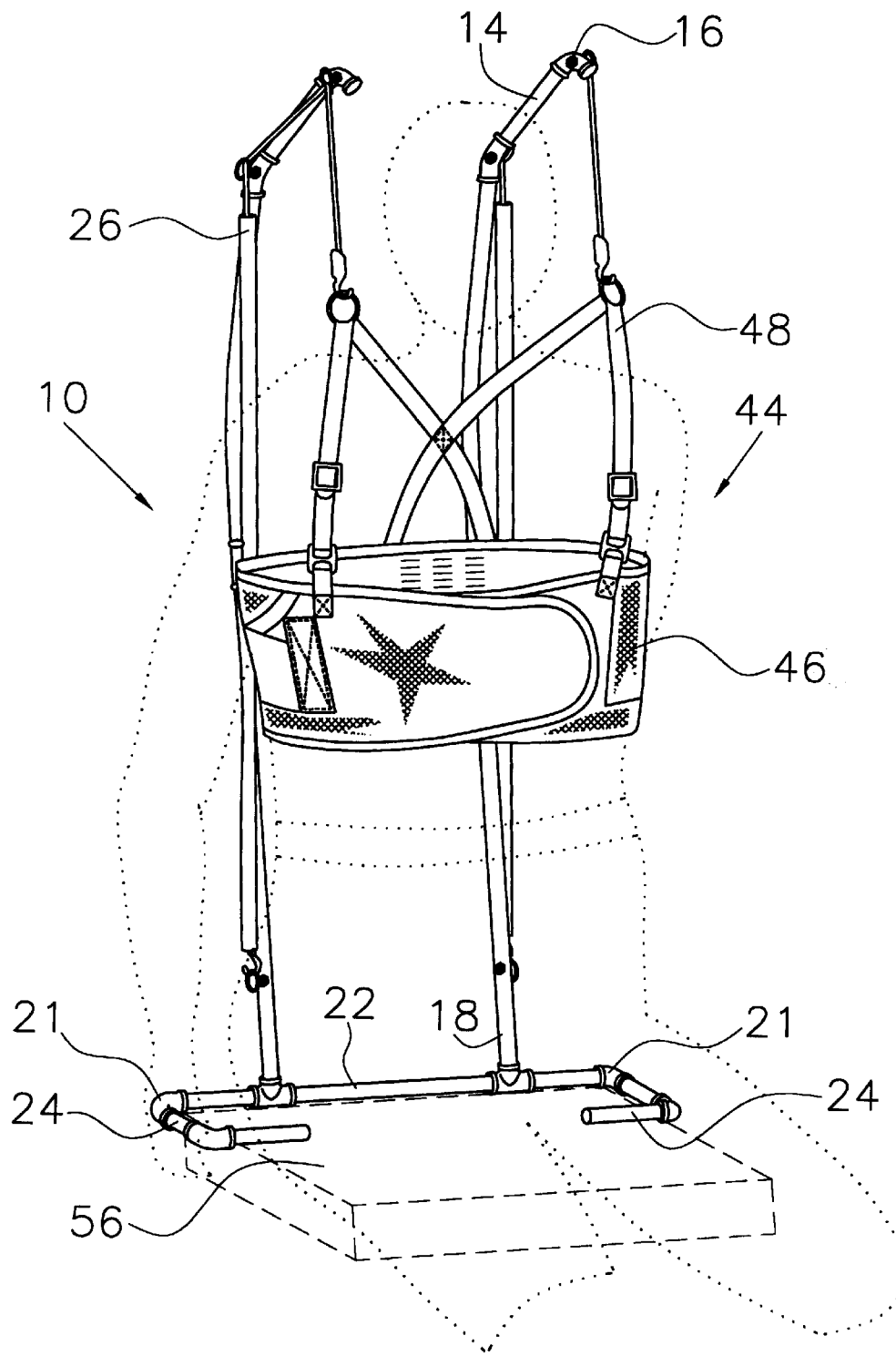
Fig.3
(AMENDED)

LOWER BACK SUPPORT APPARATUS

TECHNICAL FIELD

This invention relates to the field of devices for supporting the lower back and relieving lower back pain.

BACKGROUND ART

Back pain is one of the most common ailments affecting adults today. Back pain can be the result of different activities such as heavy lifting, standing or sitting for extended periods of time in an improper position. Many individuals have occupations which require they sit for long periods of time. If they sit in an improper position, for example slouched over, pressure on the lower back can cause a great deal of stress and pain.

Several devices have been produced to support the lower back. Typical of the art are those devices disclosed in the following U.S. patents:

| U.S. Pat. No. | Inventor(s) | Issue Date |
| --- | --- | --- |
| 4,802,667 | D. J. Altner | February 7, 1989 |
| 4,991,572 | R. L. Chases | February 12, 1991 |
| 5,387,183 | R. W. Jones | February 7, 1995 |
| 5,388,274 | Glover et al. | February 14, 1995 |
| 5,403,271 | Saunders et al. | April 4, 1995 |
| 5,421,809 | M. J. Rise | June 6, 1995 |

The 667', '183, '274, '271, and '809 patents all disclose belts worn around the waist to support the back during heavy lifting. The belts are not configured to also support the body such that the spine is aligned correctly while sitting.

The '572 patent teaches a lumbar traction device which includes an inflatable section and equalization rings secured to the support strap. The rings provide a means for suspending the device while supporting the patient in a variety of orthopedically proven positions. Although the lumbar traction device provides support for the lower back, it also does not include a means for supporting the body to align the spine correctly while sitting.

Therefore, it is an object of the present invention to provide a lower back support apparatus for supporting the lower back.

It is another object of the present invention to provide a lower back support apparatus which supports the wearer in a proper sitting position.

SUMMARY

Other objects and advantages will be accomplished by the present invention which is a lower back support apparatus for supporting an individual in a seated position. The lower back support apparatus of the present invention includes a support frame and a support belt which is supportable on the frame. The support belt defines a belt portion and straps secured to the belt portion. The belt portion is securable around the waist of a user, and the straps extend from the belt portion and are configured to fit securely on the shoulders of the user. The straps carry two rings one each positionable at each shoulder.

The support frame is configured to releasably secure to a seat. Two spring and hook assemblies mounted on opposing sides of the support frame and each includes a hook for hooking onto each of the rings.

BRIEF DESCRIPTION OF THE DRAWINGS

The above mentioned features of the invention will become more clearly understood from the following detailed description of the invention read together with the drawings in which:

FIG. 3 illustrates the lower back support apparatus as worn by an individual in a seated position.

DESCRIPTION OF PREFERRED EMBODIMENTS

A lower back support apparatus incorporating various features of the present invention is illustrated generally at 10 in the figures. The lower back support apparatus 10 is designed to support the lower back thereby relieving pain. Moreover, in the preferred embodiment, the lower back support apparatus 10 is designed to support the wearer's body in a proper sitting position.

Figure 1:
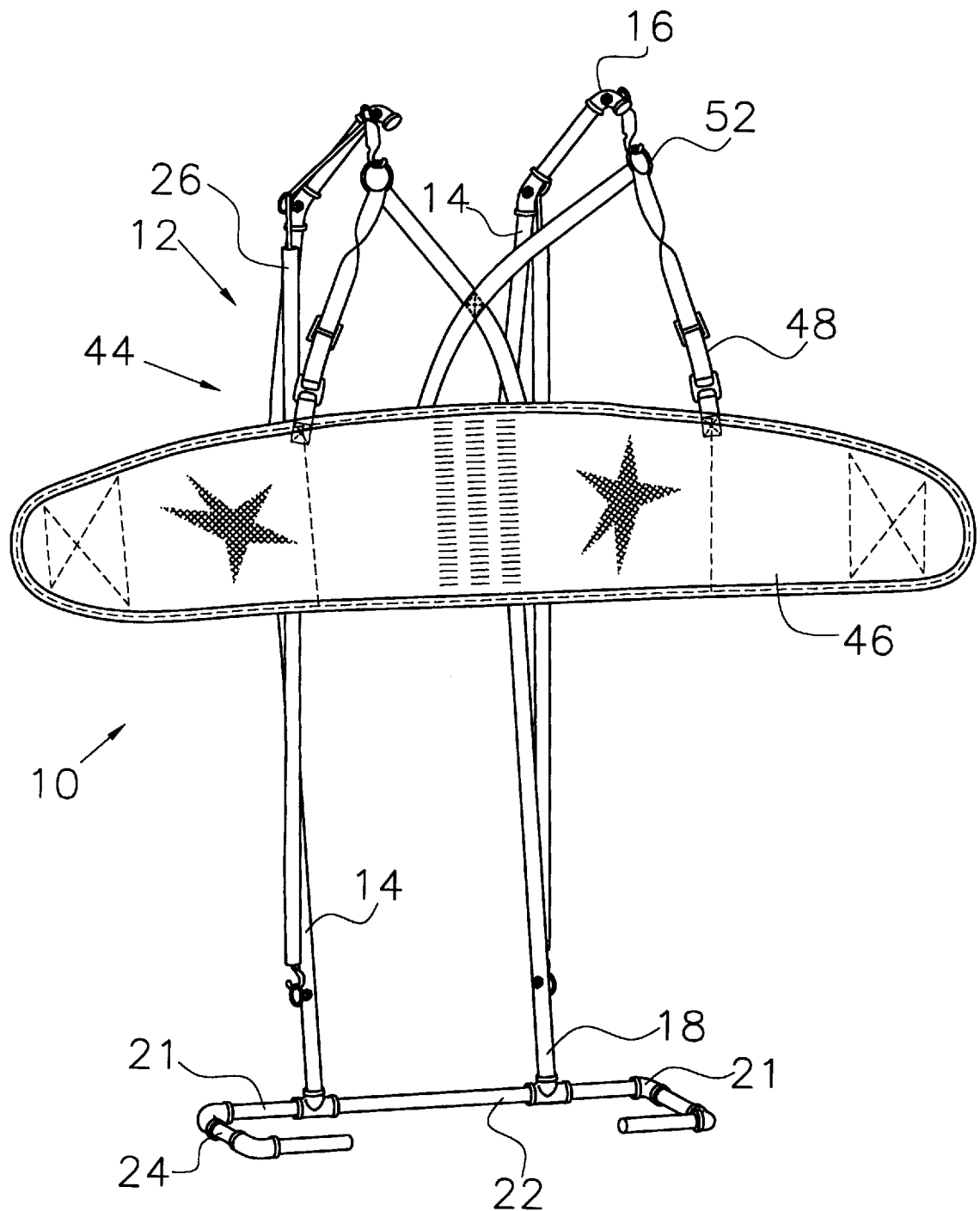
FIG. 1 is a perspective view of the lower back support apparatus constructed in accordance with several features of the present invention.

As shown in FIG. 1, the lower back support apparatus 10 is generally comprised of a support belt 44, a support frame 12 and a set of spring and hook assemblies 26 secured to opposing sides of the support frame 12. The support belt 44 is configured to be supportable on the support frame 12 via the spring and hook assemblies 26. The support frame 12, spring and hook assemblies 26 and support belt 44 work in conjunction to support the wearer's lower back and maintain the wearer in a proper, supported position.

Figure 2:
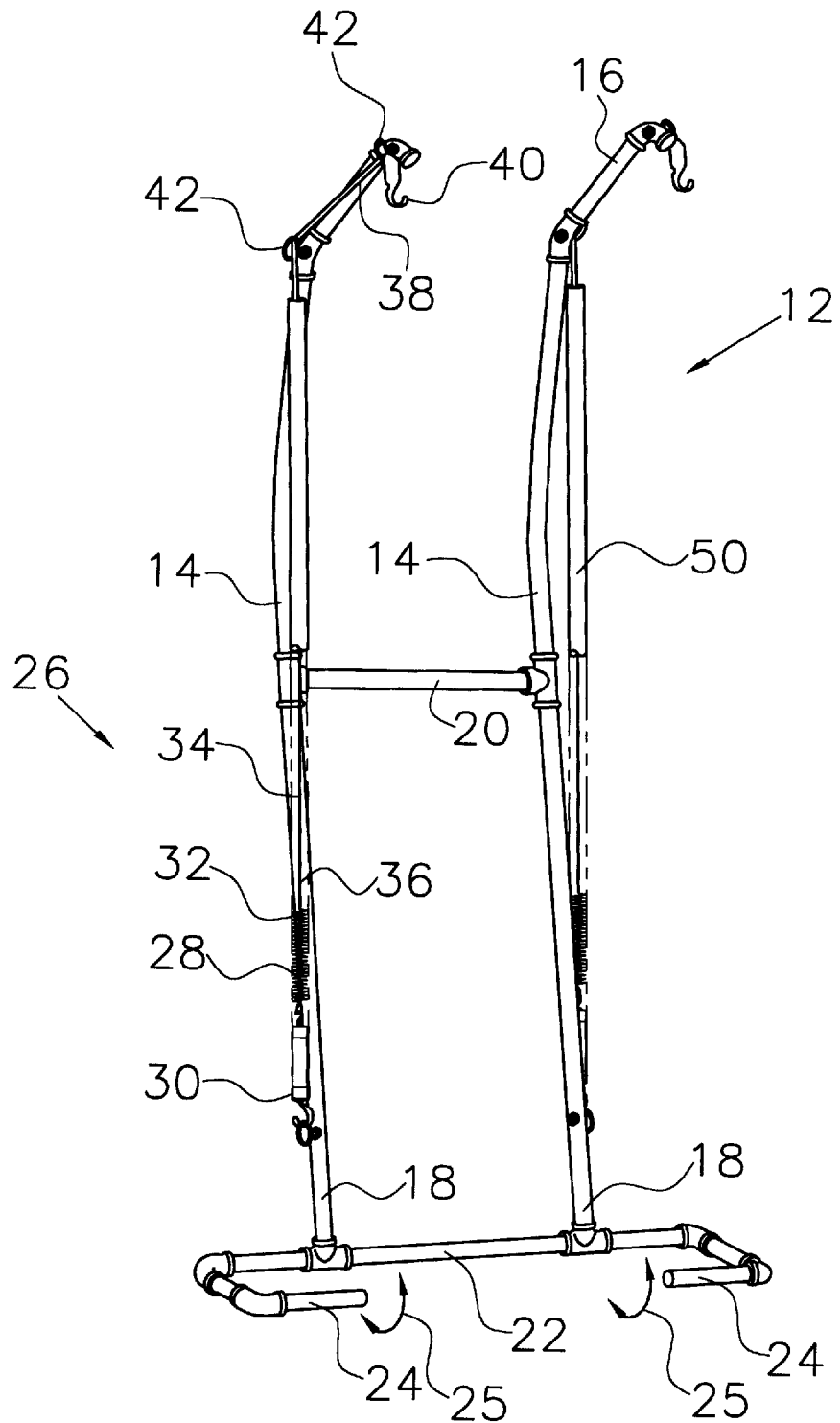
FIG. 2 is a perspective view of the support frame.

As shown in FIG. 2, the support frame 12 is an open, rectangular frame. The support frame 12 includes two upright rods 14 each of which defines a first end 16 and a second end 18. A center bar 20 extends horizontally between the rods 14 and is situated approximately halfway between the first and second ends 16, 18 of the upright rods 14. A 30 base rod 22 is secured to and extends between and beyond the second end 18 of each of the upright rods 14. In the preferred embodiment, the base rod 22 carries a swivel arm 24 at each end 21 for gripping the front 54 of a seat 56. Each swivel arm 24 is pivotable in the direction indicated by the arrow 25 and specifically, with respect to the end 21 of the base rod 22 to which the swivel arm 24 is secured, as shown in FIG. 2. In the preferred embodiment, the upright rods 14 are adjustable in length to accommodate a smaller or larger seats. Preferably, the first end 16 of each rod 14 is configured to extend over a seat. In the preferred embodiment, the upright rods 14, the center bar 20 and the base rod 22 are manufactured from a sturdy material such as plastic, PVC piping or metal.

A spring and hook assembly 26 is secured to the support frame 12. In the embodiments shown in FIGS. 1 and 2, the spring and hook assembly 26 is mounted to each of the upright rods 14. It will be noted that in an alternate embodiment, a spring and hook assembly 26 can be mounted in each of the upright rods 14. The spring and hook assembly 26 includes a tension spring 28 defining a first end 30 and a second end 32, a cord 34 defining a first end 36 of which is secured to the second end 32 of the tension spring, and a hook 40 secured to the second end 38 of the cord 34. The first end 30 of the tension spring 28 is anchored and preferably, is mounted to a respective upright rod 14 proximate the second end 18 of the upright rod 14. When the spring and hook assembly 26 is carried on exterior of the support frame 12, it is preferable to cover the spring 28 with a protective sheath 50. Further, when the spring and hook assembly 26 is carried on the exterior of the frame 12, guide eyes 42 must be secured to the upright rods 14 proximate the first end 16 for guiding the cord 34 therethrough.

In an alternate embodiment (not shown), the spring and hook assembly includes one spring from which two cords extend. Specifically, the first end of the spring is anchored to the either the center bar or the base rod. Two cords extend from the second end of the spring and each carries a hook at its end. The cords again are received through guide eyes such that the hooks extend from opposing sides of the support frame, from each upright rod.

The support belt 44 includes a belt portion 46 for securing around the wearer's waist and straps 48 secured to the belt portion 46 for fitting over the shoulder of the wearer, as shown in FIG. 2. In the preferred embodiment, the straps 48 and the belt portion 46 are adjustable to accommodate larger or smaller body frames. The straps 48 carry rings 52, one each positionable at each shoulder.

FIG. 3 illustrates an individual using the lower back support apparatus 10. Specifically, the support frame 12 is positioned to grip a seat via the swivel arms 24 of the base rod 22. The support belt 44 is secured around the waist of the user and the straps 48 are situated on the shoulders of the user. The rings 52 mounted on the straps 48 are hooked onto a respective hook 40 suspended from the first end 16 of each upright rod 14. The spring 28 defines a tension such that the individual is supported in an upright position such that pressure placed on the back while sitting is reduced.

The lower back support apparatus 10 can be used when driving without compromising safety. Further, the apparatus 10 can be used by those confined to a wheel chair. Moreover, the apparatus 10 can be used by any individual who sits for long periods of time.

From the foregoing description, it will be recognized by those skilled in the art that a lower back support apparatus offering advantages over the prior art has been provided. Specifically, the lower back support apparatus provides a means for supporting the lower back and maintaining a seated individual in an upright, proper position.

While a preferred embodiment has been shown and described, it will be understood that it is not intended to limit the disclosure, but rather it is intended to cover all modifications and alternate methods falling within the spirit and the scope of the invention as defined in the appended claims.

Having thus described the aforementioned invention, We claim:

1. A lower back support apparatus for supporting a user in a seat, said apparatus comprising:
   a support belt defining a belt portion and straps secured to the belt portion, said belt portion being configured to be securable around the waist of a user, said straps extending from said belt portion and fitting securely on the shoulders of the user, said straps carrying two rings one each positionable at each shoulder;
   a support frame defining two upright rods each defining a first end and a second end, a center bar secured to and extending between said two upright rods and a base rod secured to said second end of each of said upright rods, said base rod carrying a swivel arm at each ends each of said swivel arms being releasably secureable to a seat; and,
   a first and second spring and hook assembly each defining a first end and a second end, said first end of each of said first and second spring and hook assemblies being secured to one of said two upright rods, one each of said first and second spring and hook assemblies extending along one of said two upright rods, a second end of each of said first and second spring and hook assemblies being releasably secured to a respective one of said rings at each shoulder such that pressure on the user's back is relieved when the user is seated.

2. The lower back support apparatus of claim 1 wherein each of said first and second spring and hook assemblies includes a spring, a cord and a hook, each of said springs defining a first end and a second end, each of said cords defining a first end and a second end, said first end of each of said springs being anchored to opposing sides of said support frame, said first end of each of said cords extending from said second end of each of said springs, each of said cords being slidable with respect to each of said first ends of said upright rods, each of said hooks being secured to each of said cord second ends, one each of said hooks being securable to said rings at each shoulder of the user.

3. A lower back support apparatus for supporting a user in a seat, said apparatus comprising:
   a support belt defining a belt portion and straps secured to the belt portion, said belt portion configured to be securable around the waist of a user, said straps extending from said belt portion and configured to fit securely on the shoulders of the user, said straps carrying two rings one each positionable at each shoulder;
   a support frame defining two upright rods each defining a first end and a second end, a center bar secured to and extending between said two upright rods and a base rod secured to said second end of each of said upright rods, said base rod carrying a swivel arm at each end, each of said swivel arms being releasably securable to a seat, each of said swivel arms being pivotable with respect to said end of said base rod to which said swivel arms are securable to grip a front of the seat; and,
   a first and second spring and hook assembly each defining a first end and a second end, said first end of each of said first and second spring and hook assemblies being secured to one of said upright rods, one each of said first and second spring and hook assemblies extending along one of said two upright rods, said second end of each of said first and second spring and hook assemblies being releasably secured to a respective one of said rings at each shoulder such that pressure on the user's back is relieved when the user is seated.

4. A lower back support apparatus for supporting a user in a seat, said apparatus comprising:
   a support belt defining a belt portion and straps secured to the belt portion, said belt portion configured to be securable around the waist of a user, said straps extending from said belt portion and configured to fit securely on the shoulders of the user, said straps carrying two rings one each positionable at each shoulder;
   a support frame defining two upright rods each defining a first end and a second end, a center bar secured to and extending between said two upright rods and a base rod secured to said second end of each of said upright rods, said base rod carrying a swivel arm at each end, each of said swivel arms being releasably securable to a seat; said first end of said two upright rods adapted to extend over the seat; and,
   a first and second spring and hook assembly each defining a first end and a second end, said first end of each of said first and second spring and hook assemblies being secured to one of said two upright rods, one each of said first and second spring and hook assemblies extending along one of said two upright rods, said second end of each of said first and second spring and hook assemblies being releasably secured to a respective one of said rings at each shoulder such that pressure on the user's back is relieved when the user is seated.

* * * * *